United States Patent
Tziviskos

(10) Patent No.: US 7,837,085 B1
(45) Date of Patent: Nov. 23, 2010

(54) HERMETIC SEAL

(75) Inventor: George Tziviskos, Encino, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1427 days.

(21) Appl. No.: 10/819,610

(22) Filed: Apr. 7, 2004

Related U.S. Application Data

(60) Provisional application No. 60/461,554, filed on Apr. 9, 2003.

(51) Int. Cl.
*B23K 31/02* (2006.01)
*H01G 7/00* (2006.01)
*H01G 4/35* (2006.01)

(52) U.S. Cl. ............. 228/122.1; 228/124.6; 29/25.42; 361/302; 429/181

(58) Field of Classification Search ............. 361/536, 361/518, 302; 228/122.1, 124.6, 255; 429/181, 429/175, 176, 177; 29/25.42

See application file for complete search history.

(56) References Cited

U.S. PATENT DOCUMENTS

| | | | |
|---|---|---|---|
| 3,906,311 A * | 9/1975 | Shoot et al. ............. | 361/518 |
| 3,993,938 A * | 11/1976 | Marien et al. ............. | 361/518 |
| 4,119,363 A | 10/1978 | Camlibel et al. | |
| 5,046,242 A * | 9/1991 | Kuzma ............. | 29/878 |
| 5,241,216 A | 8/1993 | Webster | |
| 5,273,203 A | 12/1993 | Webster | |
| 5,821,011 A * | 10/1998 | Taylor et al. ............. | 429/181 |
| 5,896,267 A * | 4/1999 | Hittman et al. ............. | 361/302 |
| 6,368,451 B1 * | 4/2002 | Goulette et al. ......... | 174/152 R |
| 6,474,879 B1 | 11/2002 | Warnes et al. | |
| 6,855,456 B2 * | 2/2005 | Taylor et al. ............. | 429/181 |
| 2004/0185718 A1 * | 9/2004 | Nordquist et al. ............. | 439/620 |

* cited by examiner

*Primary Examiner*—Roy King
*Assistant Examiner*—Michael Aboagye
(74) *Attorney, Agent, or Firm*—Frommer Lawrence & Haug LLP; Bruce E. Black

(57) ABSTRACT

A seal design provides positive compression to produce a hermetic seal around a feedthrough pin in a hermetically sealed device, including an implantable medical device. One embodiment of the seal design uses a plurality of "micro-flanges" placed along the length of a feedthrough pin, which micro-flanges grabs and compresses the insulator material to form a hermetic seal. Because the seal design produces positive compression of the insulator, the seal is relatively insensitive to changes in temperature and to differences in thermal expansion coefficients ("TCEs") between the metal feedthrough and the insulator. It is therefore possible to use a wider variety of materials for the insulator and the feedthrough with the described sealing design, while achieving a superior hermetic seal.

5 Claims, 3 Drawing Sheets

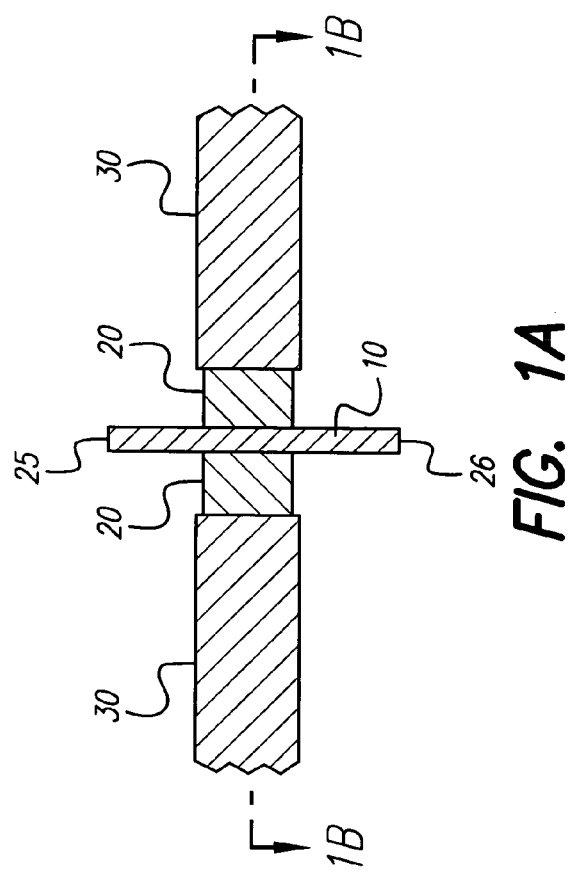
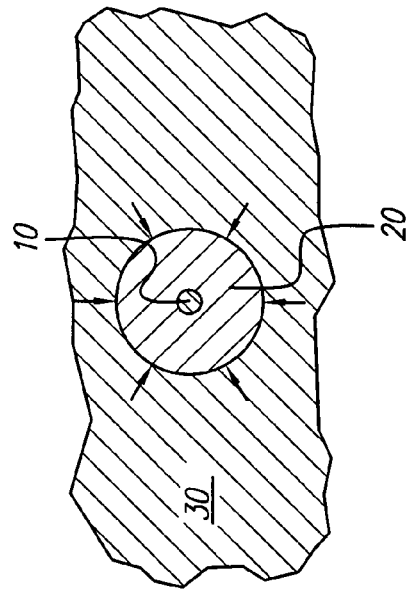

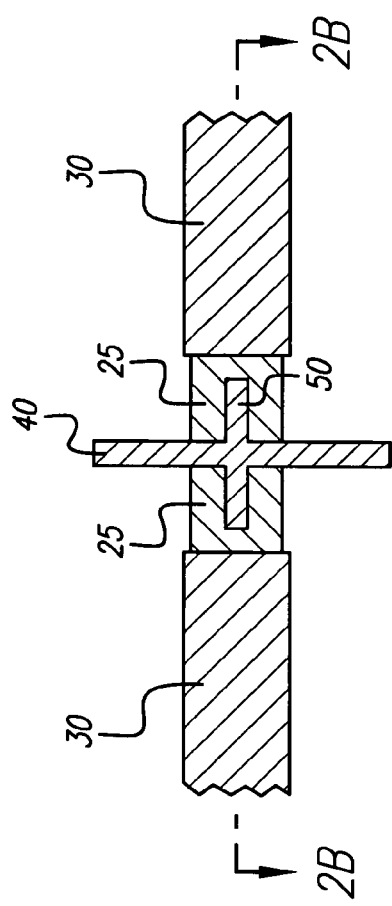
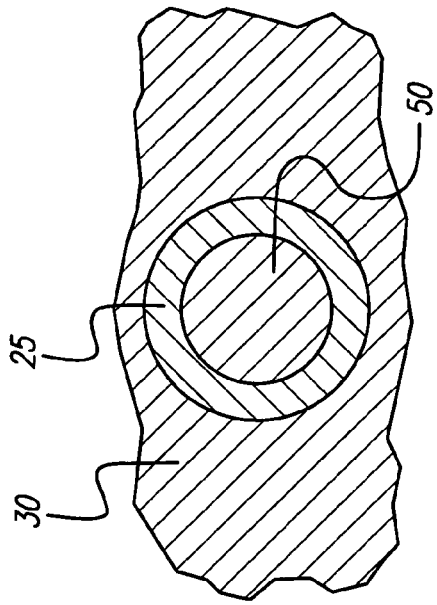
FIG. 2A
FIG. 2B

HERMETIC SEAL

The present application claims the benefit of U.S. Provisional Patent Application Ser. No. 60/461,554, filed 9 Apr. 2003, which application is herein incorporated by reference in its entirety.

BACKGROUND OF THE INVENTION

The present invention relates to hermetic seals for sealed devices and, more particularly, hermetic seals around electrical feedthrough pins.

Implantable medical devices having external leads or other electrical connections require feedthroughs that extend from the inside of the medical device to the outside. The feedthrough may be shaped as a cylindrical pin and have connectors on either end. The implantable device needs to be protected from the influx of external gases or liquids present in the body. Such influx of gases and/or liquids into the medical device may cause the device to malfunction. Therefore, the implantable medical device is typically hermetically sealed. The feedthrough exit points on the medical device housing, however, are points where the hermetic seal can be broken.

The connector pin or the feedthrough are generally made from non-corrosive metals including, but not limited to, titanium, platinum, platinum alloys such as platinum/iridium, and stainless steels.

The surrounding insulating material around the metal feedthrough, however, is typically made of glass or ceramic. Because of the difference in the thermal coefficient of expansion ("TCE") between the metal feedthrough and glass or ceramic insulator, a gap can develop between the feedthrough and the insulating glass or ceramic, thereby breaking the hermetic seal.

One method for preventing this break in the hermetic seal is to coat the metal feedthrough pin with an oxidation layer over the surface of the pin. This oxidation layer increases the adhesion between the pin surface and the insulating glass or ceramic and also increases the mean path length through the seal. Nevertheless, this method does not prevent the tendency to produce a gap between the metal pin and surrounding glass or ceramic insulation and moreover, inconsistent sealing can result because the method is fairly sensitive to manufacturing variations in the oxidation layer.

What is needed therefore is a feedthrough sealing design which positively reduces or eliminates gapping in the seal between the insulator and metal feedthrough pin.

SUMMARY OF THE INVENTION

The present invention addresses the above and other needs by providing a hermetic seal design that guarantees positive compression and therefore a positive seal, regardless of the TCE mismatch and regardless of process variations. The hermetic sealing design is also less sensitive to a broad range of operating temperatures, e.g., manufacturing temperatures, body temperatures and storage temperatures.

The present invention provides, in one aspect, a sealing system that can employ positive compression to guarantee a hermetic seal. In one embodiment, the sealing design uses at least two "flanges" that grab and compress the insulator material between the flanges to form a hermetic seal. Because the sealing design produces positive compression, the design is relatively insensitive to changes in temperature and to differences in TCE between the metal feedthrough and the insulator. Therefore, it is possible with the hermetic sealing designs of the present invention to use a wider variety of materials having different TCEs.

In one embodiment of the sealing system, the system comprises: a feedthrough pin, the pin having at least two flanges surrounding the circumference of the pin; a housing enclosing the sealed device, which housing has at least one opening; and an insulator placed within said opening of the housing. The feedthrough pin is surrounded by the insulator, hermetically sealing the opening of the housing of the sealed device.

In another embodiment of the hermetic sealing system, in accordance with the present invention, the system comprises: a feedthrough pin including at least first and second flanges emanating from the body of the feedthrough pin and an insulator surrounding the feedthrough pin. In addition, the feedthrough pin is placed under compression by the surrounding insulator, resulting in a positive hermetic seal and the feedthrough pin is part of the sealed device which is body implantable.

In yet another aspect of the present invention, a method of implementing a hermetic seal is provided. The method comprises: providing a medical device housing with a hole in the housing; providing a feedthrough pin having a first end and a second end, wherein the feedthrough pin has at least two flanges, a first flange and a second flange; and placing an insulator material within the hole and surrounding at least a portion of the feedthrough pin with the insulator material.

In one embodiment of the method, the feedthrough pin has a plurality of micro-flanges along some length of the pin. The micro-flanges are not exteriorized to the outside of the device housing but are placed into compressive contact with the insulator that surrounds the feedthrough pin.

In another embodiment of the method, the feedthrough pin has a first flange and second flange. The first flange has at least partial exposure to the outside of the device and the second flange has at least partial exposure to the inside of the device. The first and second flanges sandwich a part of insulator material therebetween in compressive contact to achieve a hermetic seal between the flanges and the insulator.

The feedthrough pin may be a biocompatible metal. The insulator that surrounds the feedthrough pin may be glass or ceramic having a thermal coefficient of expansion (TCE) which is less than the biocompatible metal of the feedthrough pin.

The feedthrough pin generally has a first end and second end. The first end is located within the device housing, whereas the second end is exteriorized to the device housing.

The feedthrough pin may have at least first and second flanges. The feedthrough pin may have at least two micro-flanges and, more preferably, a multiplicity of micro-flanges. Still yet, the feedthrough pin may have first and second flanges and micro-flanges. The insulator material is placed into a compressive contact with the micro-flanges and/or flanges to produce a hermetic seal.

It is a feature of the present invention to provide a hermetic seal in which the insulator material and metal feedthrough pin can have different TCEs.

It is another feature of the invention to provide a hermetic seal which is comparatively insensitive to precise process or manufacturing tolerances.

BRIEF DESCRIPTION OF THE DRAWINGS

The above and other aspects, features and advantages of the present invention will be more apparent from the following more particular description thereof, presented in conjunction with the following drawings wherein:

FIG. 1A shows a cut-away view of an implantable medical device housing and a conventional hermetic seal around a metal feedthrough, surrounded by an insulator;

FIG. 1B shows a partial, cross-sectional view of the medical device housing, feedthrough and insulator, as shown in FIG. 1A at line 1B-1B;

FIG. 2A shows a cut-away view of an implantable medical device housing and a conventional hermetic seal with a feedthrough pin having a single flange embedded within a surrounding insulator;

FIG. 2B shows a partial, cross-sectional view of the medical device housing, feedthrough and insulator, as shown in FIG. 2A at line 2B-2B;

Corresponding reference characters indicate corresponding components throughout the several views of the drawings.

DETAILED DESCRIPTION OF THE INVENTION

Figure 3:
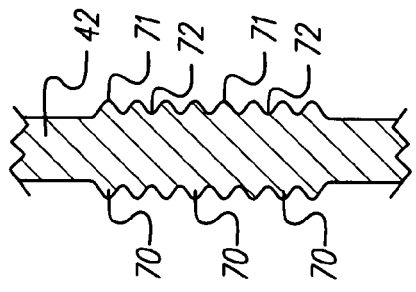
FIG. 3 shows, in accordance with the present invention, a cut-away view of an implantable medical device housing with one embodiment of the hermetic seal around a feedthrough pin, wherein compression is applied to the insulator between two, preferably circular flanges located on the feedthrough pin.

The following description is of the best mode presently contemplated for carrying out the invention. This description is not to be taken in a limiting sense, but is made merely for the purpose of describing the general principles of the invention. The scope of the invention should be determined with reference to the claims.

While the embodiments described herein refer specifically to an exemplary implantable medical device, it is emphasized that the sealing system and feedthrough device shown are applicable to any device wherein a hermetic seal is desired around a feedthrough.

FIG. 1A shows a side, cut-away view of an implantable medical device housing 30 and a conventional feedthrough pin 10 that is surrounded by an insulator 20. The insulator 20, in turn, is surrounded by an implantable medical device housing 30. Feedthrough pin 10 has two ends, a first end 25 that is inside the implantable medical device and a second end 26 that is outside the medical device. The second end 26 may have a connector which allows electrical connection to a lead that is connected to an electrode for delivering electrical stimulus pulses for stimulation of nerves.

FIG. 1B shows a partial, cross-sectional view of the medical device housing 30, the feedthrough pin 10, and the insulator 20 shown in FIG. 1A, along line 1B-1B. The insulator 20 can be glass or ceramic and can be formed around the metal feedthrough pin 10 and inside an opening in the device housing 30. The feedthrough pin 10 can be made of an implantable grade metal such as platinum, platinum alloys (such as platinum/iridium) or stainless steel. The arrows indicate compressive forces applied by the housing 30 to the circumference of the insulator 20 at the device's operating temperature range, when the housing 30 is a body compatible metal such as an implantable grade titanium. While the entire housing 30 may be made of metal, alternatively, the housing 30 may be made largely from materials other than metals. For example, in one embodiment of the housing, only the immediate area of the housing surrounding the insulator 20 and feedthrough pin 10 may be made of metal, and the rest of the housing may be ceramic. The feedthrough pin 10, the insulator 20 and the housing 30, can be made from materials having different thermal coefficients of expansions (TCEs). Metals typically have higher TCEs than ceramics or glass.

During manufacture, the feedthrough, insulator and housing may be heated to fix the feedthrough pin 10 in place relative to the device housing. As the components cool, the housing 30, which may be made of a metal having a high TCE, will shrink faster than the insulator which is usually made of glass or ceramic having a low TCE and the opening in the medical device housing 30 will compress the insulator 20.

On the other hand, the diameter of the feedthrough pin 10 will shrink more than the surrounding insulator 20 and this will tend to cause a gap between the insulator 20 and pin 10. While a compressive force may be exerted on the outer periphery of the insulator 20, such compressive force may not compensate for the tendency to gap between the feedthrough pin 10 and the insulator 20 and thus the hermetic seal can be compromised.

FIG. 2A is a side, cut-away view of a conventional feedthrough design including a single, circular flange 50 integrated as part of the feedthrough pin 40, as well as the device housing 30 and insulator 25, which insulator the flange 50 is embedded in. FIG. 2B is a cross-sectional view along line 2B-2B of FIG. 2A, showing the same medical device housing 30, flange 50 and insulator 25. As seen in FIG. 2A, the feedthrough pin 40 is surrounded by the glass or ceramic insulator 25 which also surrounds the flange 50. With the flange contained within the insulator, the feedthrough pin 40 is advantageously prevented from sliding forward or backward relative to the insulator 25. The device housing 30 typically surrounds the insulator 25. With respect to hermeticity to gases or liquids, the presence of the flange 50 increases the mean path length for a fluid or gas traveling from outside the medical device housing, through the seal, and into the medical device.

The metal feedthrough pin 40 may have a higher TCE than insulator 25, which may be made of glass or ceramic, having a lower TCE. As a result, during the cooling phase of manufacturing, the diameter of the metal feedthrough pin 40, as well as the flange 50, contracts more than the insulator 25. For the same explanation given for the conventional feedthrough design shown in FIGS. 1A and 1B, the seal between the feedthrough and insulator may gap open.

FIG. 3 shows, in accordance with the present invention, a cut-away view of a device housing 30, a feedthrough pin 41 and insulator 26. The insulator 26 may be a glass or ceramic material. A hermetic seal is created by applying compressive forces to the insulator 26 with two flanges 55 and 56 on the feedthrough pin 41. The first flange 55 and second flange may be circular in shape. The insulator 26 holds the pin 41 in place within the wall of the medical device housing 30.

The feedthrough pin 41 is typically made of a biocompatible metal and has a higher TCE compared to the insulator 26. Hence, as the feedthrough pin and surrounding insulator cools, the pin distance between the two flanges 55 and 56 decreases, thereby compressing the insulator 26 therebetween. The compression increases the tightness of the contact between flanges 55 and 56 with the insulator 26, thereby insuring a hermetic seal.

The feedthrough pin 41 may be situated so that the first flange 55, which may be circular in shape, is partly exposed, inside of the device housing 30. Further, the second flange 56, which may be circular in shape, can be partly exposed, outside of the device housing. The thickness of the insulator 26 between the first and second flanges may be variable. In one embodiment, the insulator 26 may be thinner than the wall of the device housing 30. It may be seen that the peripheral outline of the first and second flanges may be shapes other than circular, e.g., elliptical or other closed-looped shapes.

Although the embodiment of the sealing system described may be used where a sealed device is desired, the sealing system is particularly useful in body implantable medical devices.

Figure 4:
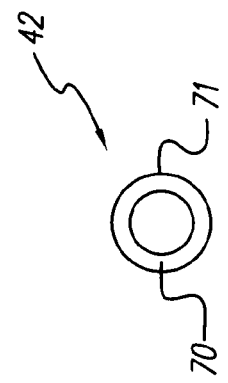
FIG. 4 shows, in accordance with the present invention, a cut-away view of an implantable medical device housing with another embodiment of a hermetic seal around a feedthrough pin, which feedthrough pin has a plurality of micro-flanges that is in compressive contact with a surrounding insulator to achieve a hermetic seal.

FIG. 4 shows, in accordance with the present invention, a side, cut-away view of an alternative embodiment of the feedthrough design which exerts compression on the insulator and thereby ensures a hermetic seal to the implantable medical device. The feedthrough pin 42, which may be made of an electrically conductive, biocompatible metal, can employ at least two and preferably a plurality of small, circular ridges or micro-flanges that circumferentially surround the surface of the feedthrough pin 42, as shown in FIG. 4. The insulator 27, which may be glass or ceramic, is formed between the metal feedthrough pin 42 and the device housing 30. The ridges of the micro-flanges in the metal pin 42 are placed into compressive contact with the insulator 27 and this helps to stabilize the pin 42 and prevents forward and backward movements along the axis of the feedthrough pin relative to the insulator 27. The feedthrough pin 42, which may be made of a biocompatible metal, may have a higher TCE compared to the insulator 26.

It can be seen that the feedthrough pin is an elongate configuration having a first end and a second end. The first end may be placed inside the device housing 30. The second end may be exteriorized to outside of the device housing 30. The second end may be further attached to an electrical connector which can be used to connect to a stimulation lead.

Figure 5A:
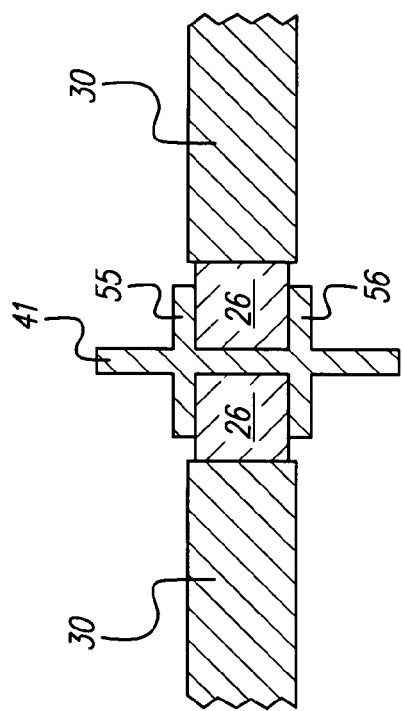
FIG. 5A shows, in accordance with the present invention, an enlarged, cross-sectional, side view of the feedthrough pin shown in FIG. 4, depicting the micro-flanges.
Figure 5B:
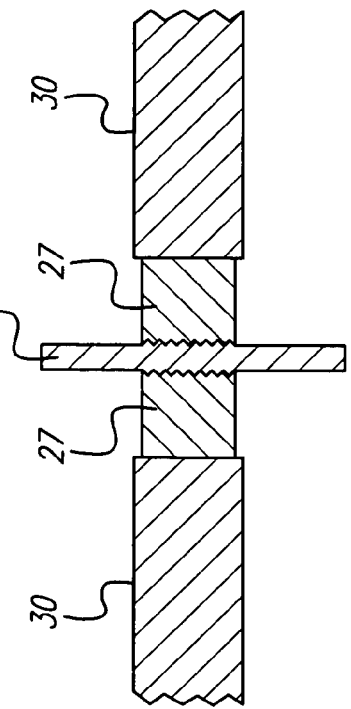
FIG. 5B shows, in accordance with the present invention, a bottom view of the feedthrough pin of FIG. 5A.

FIG. 5A shows a cross-sectional, enlarged view of the feedthrough pin 42 of FIG. 4, with the view showing the curved shape of the ridges or micro-flanges 70. FIG. 5B depicts a bottom view of the pin 42 of FIG. 5A. FIG. 5A shows that the micro-flanges 70 are comprised of convex ridges 71 and concave troughs 72 between at least two adjacent micro-flanges. Each ridge preferably has no discontinuities, i.e., sharp edges, as sharp edges might encourage propagation of microcracks. In addition, it is preferably that the troughs also are gently curved as to have no sharp discontinuities, as they could be points for crack propagation in the feedthrough pin. Each micro-flange preferably fully encircles the outer circumference of the feedthrough pin 42 along the length of the pin. Preferably, there is a multiplicity of ridges or micro-flanges all along the length of the feedthrough pin.

The feedthrough design, shown in FIGS. 4, 5A and 5B, provides a compressive, hermetic seal between adjacent micro-flanges 70 and insulator 27. During manufacture, both the insulator, which may be glass or ceramic, and the metal feedthrough pin are heated as the insulator is conformed around the pin. The differential in TCEs between the metal feedthrough pin 42 and the insulator 27 causes the length of the feedthrough pin to contract more than the insulator, as the components are cooled. As a result of this differential contraction, the insulator 27 is grabbed between two micro-flanges 70, placing the insulator under compression. This compression can positively maintain a hermetic seal between the feedthrough pin 42 and the insulator 27. As shown in FIG. 5A, the degree of the convex and concave curvatures defining the ridges, the depth of the trough, and the peak-to-peak width between ridges 71 may be adjusted to prevent propagation of cracks in the insulator 27 (shown in FIG. 4) as the micro-flanges are in compressive contact with the insulator. As previously discussed, a hermetic seal between the metal housing 30 and the insulator 27 may be achieved because the metal housing 30 contracts around the insulator 27, thereby placing the periphery of the insulator under compression.

It is emphasized that the embodiment of the sealing system thus described may be used where a sealed device is desired, but the sealing system is particularly useful in body implantable medical devices.

In sum, in one embodiment, the present invention provides a hermetic sealing system comprising: a feedthrough pin, the pin having at least two flanges surrounding the circumference of the pin; a housing enclosing the sealed device, which housing has at least one opening; and an insulator placed within said opening of the housing, wherein the feedthrough pin is surrounded by the insulator hermetically sealing the opening of the housing of the sealed device. In another embodiment, the feedthrough pin has a multiplicity of micro-flanges, instead of at least two flanges. The micro-flanges are placed into compressive contact with a ceramic or glass insulator and provides a hermetic seal. In yet another embodiment, the feedthrough pin has at least two larger flanges and also micro-flanges.

In another aspect of the invention, a method for implementing a hermetic seal is provided. The method comprises: providing a medical device housing with a hole in the housing; providing a feedthrough pin having a first end and a second end, wherein the feedthrough pin has at least two flanges, a first flange and a second flange; and placing an insulator material within the hole and surrounding at least a portion of the feedthrough pin with the insulator material. The feedthrough pin is then placed in a compressive contact with the insulator to achieve a hermetic seal. In another embodiment of the method, the feedthrough pin may use micro-flanges only. In still another embodiment of the method, the feedthrough pin may employ both large flanges and micro-flanges in combination.

While the invention herein disclosed has been described by means of specific embodiments and applications thereof, numerous modifications and variations could be made thereto by those skilled in the art without departing from the scope of the invention set forth in the claims.

What is claimed is:

1. A hermetic sealing system for a sealed medical device, the system comprising:
   a feedthrough pin forming a unit piece comprising at least a first flange and a second flange, and wherein the entire feedthrough pin, including the first and second flanges, is formed of a biocompatible metal;

a housing enclosing the sealed medical device, wherein said housing has at least one opening; and an insulator placed within said opening of the housing, the insulator having an interior surface and an exterior surface opposite the interior surface, wherein at least a portion of the insulator is compressed between the first and second flanges, wherein the feedthrough pin is surrounded by the insulator hermetically sealing the opening of the housing of the sealed medical device and wherein the first flange is disposed over at least a portion the interior surface of the insulator and the second flange is disposed over at least a portion of the exterior surface of the insulator.

2. The system of claim 1,
wherein the insulator is selected from the group consisting of glass and ceramic; and
wherein the thermal coefficient of expansion of the insulator is less than the feedthrough pin.

3. The system of claim 1, wherein the feedthrough pin has a first end located within the sealed medical device housing and a second end which is outside the sealed medical device housing.

4. The system of claim 1, wherein the first and second flanges are circular.

5. The system of claim 1, wherein the hermetically sealed medical device is implantable in a body of a person.

* * * * *